United States Patent [19]

Kimura et al.

[11] Patent Number: 5,048,093
[45] Date of Patent: Sep. 10, 1991

[54] DEFECT COUNTING METHOD AND APPARATUS

[75] Inventors: Hiroaki Kimura; Masaki Fuse; Masatoshi Toda, all of Kawasaki, Japan

[73] Assignee: Mitsubishi Rayon Company, Ltd., Tokyo, Japan

[21] Appl. No.: 507,492

[22] Filed: Apr. 11, 1990

[30] Foreign Application Priority Data

Apr. 13, 1989 [JP]  Japan .................................. 1-93667

[51] Int. Cl.$^5$ ............................................. G06K 9/46
[52] U.S. Cl. ........................................... 382/8; 382/25
[58] Field of Search ........................ 356/237; 358/106; 382/8, 25; 377/10, 11

[56] References Cited

U.S. PATENT DOCUMENTS

| 4,741,044 | 4/1988 | Polomsky et al. | 358/106 |
| 4,758,782 | 7/1988 | Kobayashi | 358/106 |
| 4,809,341 | 2/1989 | Matsui et al. | 358/106 |
| 4,845,558 | 7/1989 | Tsai et al. | 358/106 |

*Primary Examiner*—Leo H. Boudreau
*Attorney, Agent, or Firm*—Oblon, Spivak, McClelland, Maier & Neustadt

[57] ABSTRACT

In a defect counting method and apparatus, a projection or a corner of a defect area is successively identified from a pixel and pixels close to the pixel, especially, from four pixel groups. The number of the defect areas is incremented when the projection is identified and decremented when the corner is identified.

14 Claims, 3 Drawing Sheets

| SHAPE | SIZE | EXAMPLE |
|---|---|---|
| CONVEX | SMALL |  |
| | LARGE |  |
| CONCAVE | SMALL |  |
| | LARGE |  |

| SHAPE | SIZE | EXAMPLE |
|---|---|---|
| CONVEX | SMALL |   |
| | LARGE |  |
| CONCAVE | SMALL |     |
| | LARGE |   |

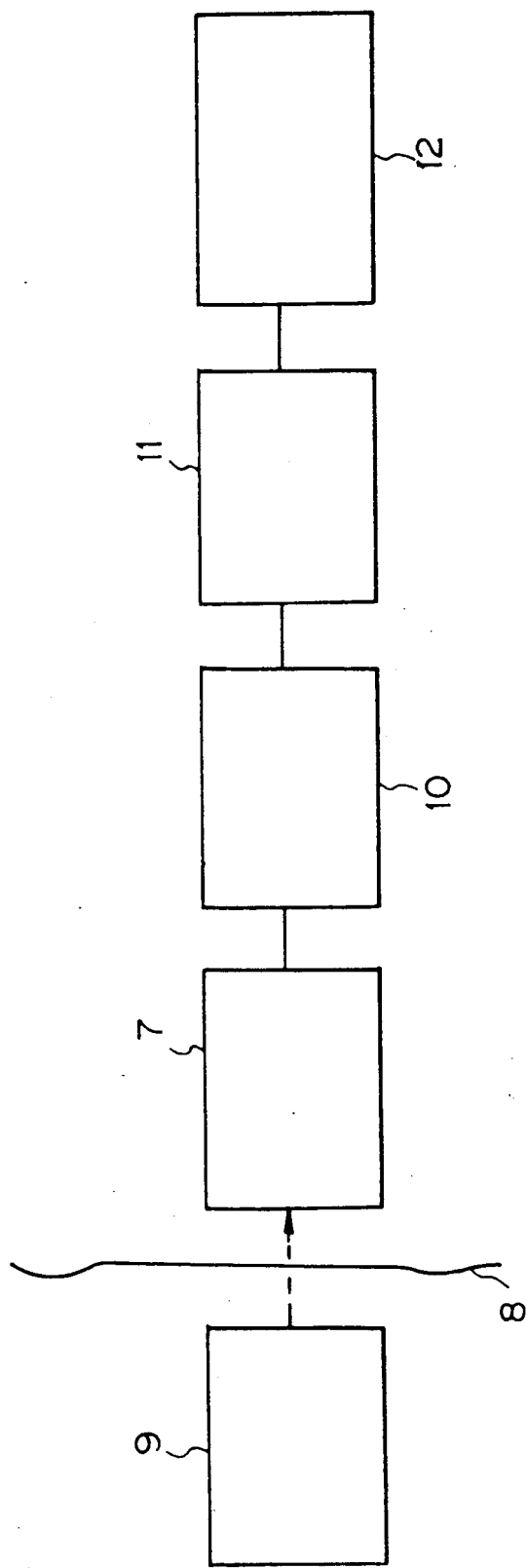

DEFECT COUNTING METHOD AND APPARATUS

BACKGROUND OF THE INVENTION

1. Field of the Invention

The present invention relates to a defect counting method and apparatus for counting defect areas such as alien substances, spots, stains, dirt marks, dark spots, pinholes, and fish eyes on tested objects, by counting images of the defect areas contained in image data of the object detected by a sensor device such as a line CCD camera.

2. Description of the Related Art

Conventionally, a so-called labelling method is applied to count defect areas such as alien substances, spots, stains, dirt marks, dark spots, pinholes, and fish eyes contained in image data. The labelling method is a method wherein a label (name) is assigned to "1" pixels constituting a continuous area and another different label is assigned to "1" pixels constituting another continuous area, in a binary image. The method comprises a procedure wherein the same label is propagated to a neighboring "1" pixel and a procedure wherein if a continuous area encounters another continuous area having a different label, then a label of one area is replaced with that of another area.

In the counting method utilizing the labelling method, the binary image is scanned until a pixel having a value "1" is found. When a pixel having the value "1" is found, the value of the pixel is changed from "1" to "$\mu$" which is a minimum value among unused values for labelling. Next, the scanning process is continued. If a pixel having the value "1" and neighboring the pixel to which the label "$\mu$" has been assigned is found, the value of the found pixel is changed from "1" to "$\mu$", if a pixel having the value "1" and not neighboring any pixel to which any label has been assigned, the value of the found pixel is changed from "1" to "$\mu+1$" for new labelling, and the processes are repeated.

When the scanning process is finished, the value of the newest label corresponds to the number of the defect areas, namely, the number of the defect areas such as the alien substances, spots, strains, dirt marks, dark spots, pinholes, and fish eyes on the tested object.

However, in a defect counting method and apparatus using the aforementioned labelling, a memory capable of storing a large number is required for each pixel, and additionally, as the maximum value of the count is determined by the size of the memory, for example, if the memory has the size of 8 bits/pixel, the count can only go up to 256.

SUMMARY OF THE INVENTION

It is an object of the present invention to provide a defect counting method and apparatus which can count images of defect areas contained in image data of a tested object detected by a sensor device and which does not require a large size memory for each pixel.

In accordance with the present invention there is provided a defect counting method for measuring the number of defect areas contained in binary image data comprising the steps of:

i) inputting values of a first pixel and second pixels close to the first pixel from among the binary image data, ii) identifying a projection or a corner of a defect area from the values of the first and second pixels, iii) incrementing the number of the defect areas when the projection is identified, iv) decrementing the number of the defect areas when the corner is identified, and v) repeating steps i) to iv) selecting each pixel constituting the binary image as said first pixel.

In accordance with the present invention there is also provided a defect counting apparatus for measuring the number of defect areas contained in binary image data, comprising a storing means for storing at least values of a first pixel and second pixels close to the first pixel from among the binary data wherein the contents of the storing means are renewed selecting each pixel constituting the binary image as said first pixel, an identification means for identifying a projection or a corner of a defect area from values of the first and second pixels stored in the storing means, and a counter means for counting the defect areas wherein the counter means is incremented when the projection is identified in the identification means and decremented when the corner is identified in the identification means.

BRIEF DESCRIPTION OF THE DRAWINGS

FIG. 3 is a schematic block diagram of a system including an apparatus according to the present invention for testing a transparent film.

DESCRIPTION OF THE PREFERRED EMBODIMENTS

The preferred embodiments of the present invention will be described with reference to the accompanying drawings, but the present invention is not restricted to the embodiments as long as it does not exceed the scope of the claims.

In the preferred embodiments, each pixel (i, j) which is successively scanned is tested with two pixels (i−1, j) and (i, j−1) neighboring the scanned pixel (i, j) and a pixel (i−1, j−1) neighboring the two pixels (i−1, j) and (i, j−1). A projection or a corner having a predetermined shape of a defect area in a binary image is identified based on the values of the four pixels. If the projection is identified, the count of the defect areas is incremented, and if the corner is identified, the count of the defect areas is decremented.

In an algorithm for counting the defect areas in an embodiment of the present invention, the projection is identified only when the value of the pixel (i, j) is "1" and the others are "0" among the four pixels and the corner is identified only when the value of the pixel (i−1, j−1) is "0" and the others are "1". Table I shows this algorithm. "1" shows a pixel belonging to the defect area and "0" shows a pixel not belonging to the defect area among four pixels shown in a 2×2 matrix.

TABLE I

| Algorithm in the Present Embodiment | | |
|---|---|---|
| identification | conditions | count |
| projection | j−1 [ 0 \| 0 ]<br>j  [ 0 \| 1 ]<br>   i−1   i | +1 |

TABLE I-continued

| Algorithm in the Present Embodiment | | |
|---|---|---|
| identification | conditions | count |
| corner | $j-1$ `[0][1]` <br> $j$ `[1][1]` <br> $i-1$ $i$ | −1 |

Figure 1:
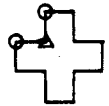
FIG. 1 is a diagram showing several examples of defective areas to which a defect counting method according to the present invention is applied.
Figure 1:
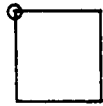
Figure 1:
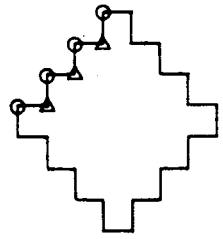
Figure 1:
Figure 1:
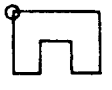
Figure 1:
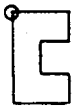
Figure 1:
Figure 1:
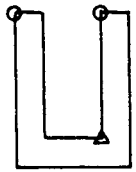
Figure 1:

FIG. 1 shows results obtained from the algorithm of the embodiment in several patterns of the defect areas. The patterns are classified according to their shape (convex or concave) and the number of the pixels constituting the patterns. The white circle mark and white triangle mark shown in FIG. 1 correspond to the positions of the projection and the corner, respectively, identified according to the algorithm of the embodiment. The number of the defect areas is calculated by subtracting the number of the white triangle marks from the number of the white circle marks. It is evident from the figure that in all the patterns shown in FIG. 1, the number of the defect area is decided as one.

As seen from the examples shown in FIG. 1, generally, under certain conditions, the number of projections is more than that of corners by one in a defect area. Accordingly, the number of the defect areas can be calculated by subtracting the number of corners from the number of the projections.

Figure 2:
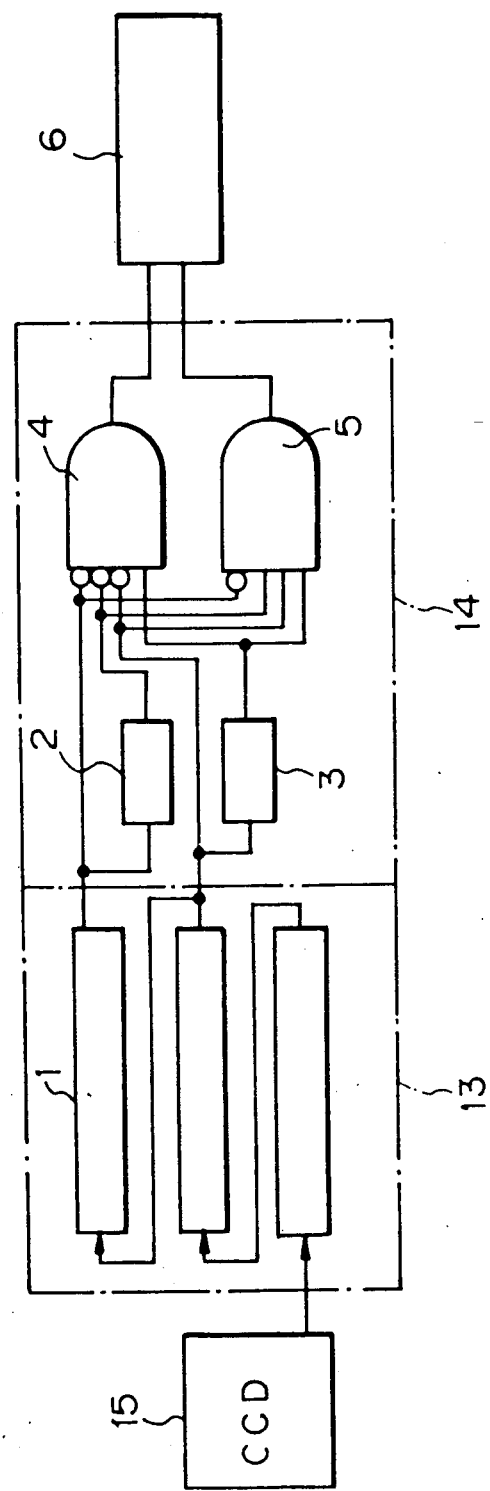
FIG. 2 is a circuit diagram of a defect counting apparatus according to the present invention.

FIG. 2 shows an example of a circuit construction for successively performing the algorithm of the embodiment.

The circuit comprises a storing means 13 which consists of a buffer memory 1 which is a shift register storing m rows (the number of CCD elements)×3 columns of binary image data obtained from CCD (Charge Coupled Device) 15, delay circuits 2 and 3 for delaying a signal by a pixel, an AND circuit 4 which outputs a logic "1" only when the value of the pixel (i, j) is logic "1" and the others are logic "0" among the four pixels (i, j), (i−1, j), (i, j−1), and (i−1, j−1), an AND circuit 5 which outputs a logic "1" only when the value of the pixel (i−1, j−1) is logic "0" and the others are logic "1", and a counter 6 which is incremented when the output of the AND circuit 4 is logic "1" and decremented when the output of the AND circuit 5 is logic "1". The buffer memory 1, delay circuits 2 and 3, and the AND circuits 4 and 5 constitute an identification circuit 14.

The circuit shown in FIG. 2 operates as follows. The binary image data obtained from the CCD 15 is input to the buffer memory 1. The buffer memory 1 stores m rows×3 columns of data. The binary data in (j−1) and (j) column stored in the buffer memory 1 is input to the AND circuits 4 and 5 and the binary data delayed in the delay circuits 2 and 3 by a pixel is also input to the AND circuits 4 and 5. The counter 6 is incremented when the output from the AND circuit 4 is logic "1", and decremented when the output from the AND circuit 5 is logic "1". Next, the aforementioned counting process is repeated from 2 to m in i and from 2 to m in j while the image data obtained from CCD 15 is successively input to the buffer memory 1.

FIG. 3 shows a construction of an apparatus where an example of the defect counting apparatus according to the present invention is applied for the testing of defects of transparent films. The system shown in FIG. 3 is constructed from a linear light source 9, a line CCD 7 facing the light source 9, a film 8 interposed between the light source 9 and the CCD 7, an A/D converter 10 for receiving the output from the CCD 7, a comparator 11 for receiving a digital output from the A/D converter 10, and a defect counting apparatus 12 according to the aforementioned embodiment.

In the system shown in FIG. 3, a picture image is formed by projecting light from a linear light source 9 through a film 8 to a line CCD 7. Image data obtained in an 8 bit A/D converter 10 is translated to binary codes in a comparator 11. The binary image data is input to a defect counting apparatus 12 to be handled as explained in the aforementioned embodiment. Photographic conditions in the line CCD camera 7 are shown in Table II.

TABLE II

| Photographic Conditions of a Line CCD Camera | |
|---|---|
| items | condition |
| number of elements | 2048 |
| clock frequency | 20 MHz |
| scanning interval | 0.2 msec |
| resolution | 0.5 mm |
| visual field | 1024 mm |

Fish eyes having more than 0.2 mmϕ contained in a transparent film were counted according to the embodiment. Though the size of the pixel was 0.5 mm square, the fish eyes were exactly detected since images including surrounding portions formed by optical distortion were detected.

The present invention is not restricted to the aforementioned embodiment, but various kinds of modulation may be realized.

For example, the counting process may be realized in an algorithm where the counter is incremented when only the pixel (i−1, j) has a value of "1" and the others have values of "0" among the input four pixels (i, j), (i−1, j), (i, j−1) and (i−1, j−1) and decremented when only the pixel (i, j−1) has a value of "0" and the others have value of "1", as shown in Table III.

TABLE III

| Algorithm in a Modulated Example | | |
|---|---|---|
| identification | conditions | count |
| projection | $j-1$ `[0][0]` <br> $j$ `[1][0]` <br> $i-1$ $i$ | +1 |
| corner | $j-1$ `[1][0]` <br> $j$ `[1][1]` <br> $i-1$ $i$ | −1 |

Additionally, the counting process may also be realized in an algorithm where the counter is incremented when only the pixel (i−1, j−1) has a value of "1" and the others have values of "0" among the input four pixels (i, j), (i−1, j), (i, j−1) and (i−1, j−1) and decremented when only the pixel (i, j) have a value of "0" and the others have values of "1", as shown in Table IV.

TABLE IV

| Algorithm in Another Modulated Example | | |
|---|---|---|
| identification | conditions | count |
| projection | $j-1$ `[0][0]` <br> $j$ `[1][0]` <br> $i-1$ $i$ | +1 |

TABLE IV-continued

Algorithm in Another Modulated Example

| identification | conditions | count |
|---|---|---|
| corner | j−1: [1][1]<br>j: [1][0]<br>    i−1 i | −1 |

Furthermore, the counting process may also be realized in an algorithm where the counter is incremented when only the pixel (i, j−1) has a value of "1" and the others have values of "0" among the input four pixels (i, j), (i−1, j), (i, j−1) and (i−1, j−1) and decremented when only the pixel (i−1, j) has a value of "0" and the others have values of "1", as shown in Table V.

TABLE V

Algorithm in Another Modulated Example

| identification | conditions | count |
|---|---|---|
| projection | j−1: [0][1]<br>j: [0][0]<br>    i−1 i | +1 |
| corner | j−1: [1][1]<br>j: [0][1]<br>    i−1 i | −1 |

The present invention is not restricted in the aforementioned embodiments, but various kinds of modulation may be realized.

For example, if memories having sufficient size are available, the four pixel data may be input from a required location of n × m image data stored in the memories to the identification circuit 14, so that the defect counting is performed.

As demonstrated in the aforementioned examples, the defect counting method and the defect counting apparatus according to the present invention provide the following effects.

i) A memory capable of storing a large number is not required for each pixel as required in the prior art utilizing the labelling method, so that the defect counting can be economically carried out.

ii) The maximum value of the count is not determined by the size of the memory for labelling each pixel, but is determined by the size of the counter. Therefore, a great many defect areas can be counted only by increasing the size of the counter to a sufficient size.

iii) As each counting process is carried out regarding a local four pixels, the method is advantageous in data processing.

iv) In the preferred embodiment of the present invention, the process is successively carried out, so that real time process of the binary data from the sensor such as the CCD can be effectively realized.

v) Each defective area having a convex or concave shape can be identified so that the method is effective in measurement of the number of the defective areas.

We claim:

1. A defect counting method for measuring the number of defect areas contained in binary image date comprising the steps of:
   i) scanning the binary image date;
   ii) inputting into a memory values of a first pixel and second pixels close to the first pixel from among the binary image data;
   iii) identifying a projection or a corner of a defect area from said values of the first and second pixels;
   iv) incrementing, in a counter, a number of the defect areas when each projection is identified;
   v) decrementing, in the counter, the number of the defect areas when each corner is identified; and
   vi) repeating said steps i) to v) selecting each pixel constituting the binary image as said first pixel.

2. A defect counting method as claimed in claim 1, wherein said binary image data is formed as a m×n matrix and said repeating process is successively carried out on said m×n matrix.

3. A defect counting method as claimed in claim 2, wherein said second pixels include two third pixels both of which are neighboring said first pixel and another pixel, and a fourth pixel which is neighboring said two third pixels, said projection of the defect area being identified when the value of the first pixel is logic "1" and the values of the third and fourth pixels are logic "0", and said corner of the defect area is identified when the value of the fourth pixel is logic "0" and the values of the first and third pixels are logic "1".

4. A defect counting method as claimed in claim 3, wherein an element [i, j] of said m×n matrix is assigned to said first pixel, elements [i−1, j] and [i, j−1] of said m×n matrix are assigned to said two third pixels, and an element [i−1, j−1] of said m×n matrix is assigned to said fourth pixel, wherein i and j satisfy the relationships 2≦i≦m and 2≦j≦n.

5. A defect counting method as claimed in claim 3, wherein an element [i−1, j] of said m×n matrix is assigned to said first pixel, elements [i−1, j−1] and [i, j] of said m×n matrix are assigned to said two third pixels, and an element [i, j−1] of said m×n matrix is assigned to said fourth pixel, wherein i and j satisfy the relationships 2≦i≦m and 2≦j≦n.

6. A defect counting method as claimed in claim 3, wherein an element [i−1, j−1] of said m×n matrix is assigned to said first pixel, elements [i−1, j] and [i, j−1] of said m×n matrix are assigned to said two third pixels, and an element [i, j] of said m×n matrix is assigned to said fourth pixel, wherein i and j satisfy the relationships 2≦i≦m and 2≦j≦n.

7. A defect counting method as claimed in claim 3, wherein an element [i, j−1] of said m×n matrix is assigned to said first pixel, elements [i, j] and [i−1, j−1] of said m×n matrix are assigned to said tow third pixels, and an element [i−1, j] of said m×n matrix is assigned to said fourth pixel, wherein i and j satisfy the relationships 2≦i≦m and 2≦j≦n.

8. A defect counting apparatus for measuring the number of defect areas contained in binary image data comprising
   a storing means for storing at least values of a first pixel and second pixels close to the first pixel from among the binary data wherein the contents of said storing means are renewed selecting each pixel constituting the binary image as said first pixel,
   an identification means for identifying a projection or a corner of a defect area from values of the first and second pixels stored in said storing means, and
   a counter means for counting the defect areas wherein the counter means is incremented when the projection is identified in said identification means and decremented when the corner is identified in said identification means.

9. A defect counting apparatus as claimed in claim 8, wherein said binary image data is formed as a m×n matrix and the contents of said storing means are renewed by successively selecting each element of said m×n matrix as said first pixel.

10. A defect counting apparatus as claimed in claim 9, wherein said second pixels include two third pixels both of which are neighboring said first pixel and another pixel, and a fourth pixel which is neighboring said two third pixels, said projection of the defect area being identified when the value of the first pixel is logic "1" and the values of the third and fourth pixels are logic "0", and said corner of the defect area is identified when the value of the fourth pixel is logic "0" and the values of the first and third pixels are logic "1", in said identification means.

11. A defect counting apparatus as claimed in claim 10, wherein an element [i, j] of said m×n matrix is assigned to said first pixel, elements [i−1, j] and [j, j−1] of said m×n matrix are assigned to said two third pixels, and an element [i−1, j−1] of said m×n matrix is assigned to said fourth pixel, wherein i and j satisfy the relationships $2 \leq i \leq m$ and $2 \leq j \leq n$.

12. A defect counting apparatus as claimed in claim 10, wherein an element [i−1, j] of said m×n matrix is assigned to said first pixel, elements [i−1, j−1] and [i, j] of said m×n matrix are assigned to said two third pixels, and an element [i, j−1] of said m×n matrix is assigned to said fourth pixel, wherein i and j satisfy the relationships $2 \leq i \leq m$ and $2 \leq j \leq n$.

13. A defect counting apparatus as claimed in claim 10, wherein an element [i−1, j−1] of said m×n matrix is assigned to said first pixel, elements [i−1, j] and [i, j−1] of said m×n matrix are assigned to said two third pixels, and an element [i, j] of said m×n matrix is assigned to said fourth pixel, wherein i and j satisfy the relationships $2 \leq i \leq m$ and $2 \leq j \leq n$.

14. A defect counting apparatus as claimed in claim 10, wherein an element [i, j−1] of said m×n matrix is assigned to said first pixel, elements [i, j] and [i−1, j−1] of said m×n matrix are assigned to said two third pixels, and an element [i−1, j] of said m×n matrix is assigned to said fourth pixel, wherein i and j satisfy the relationships $2 \leq i \leq m$ and $2 \leq j \leq n$.

* * * * *